United States Patent [19]

Skuballa et al.

[11] 4,346,228
[45] Aug. 24, 1982

[54] NOVEL 11-OXOPROSTAGLANDIN DERIVATIVES

[75] Inventors: Werner Skuballa; Bernd Raduechel; Helmut Vorbrueggen; Walter Elger; Olaf Loge; Eckehard Schillinger, all of Berlin, Fed. Rep. of Germany

[73] Assignee: Schering Aktiengesellschaft, Bergkamen, Fed. Rep. of Germany

[21] Appl. No.: 677,420

[22] Filed: Apr. 15, 1976

[30] Foreign Application Priority Data

Apr. 18, 1975 [DE] Fed. Rep. of Germany ....... 2517773

[51] Int. Cl.³ .......................................... C07C 177/00
[52] U.S. Cl. ..................................... 560/53; 560/121; 562/463; 562/464; 562/503; 564/169; 564/171; 549/71; 424/308; 424/317; 549/414; 549/415; 549/420; 549/475
[58] Field of Search .................. 260/473; 560/121, 53; 562/503, 463, 464; 564/169, 171; 549/71

[56] References Cited

PUBLICATIONS

Derwent Abstract 73279U-B NL-7306462-Q (11-1-3-73).

Primary Examiner—Paul J. Killos
Attorney, Agent, or Firm—Millen & White

[57] ABSTRACT

11-Oxoprostaglandin derivatives of the formula

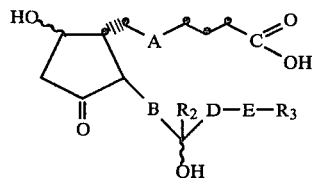

wherein $R_2$ is a hydrogen atom or alkyl of 1–5 carbon atoms,
$R_3$ is alkyl of 1–5 carbon atoms, alkylaryl, cycloalkyl of 5–6 ring carbon atoms and a total of 5–10 carbon atoms; benzodioxol-2-yl, phenyl, naphthyl or phenyl or naphthyl substituted by phenyl, halogen, alkyl of 1–4 carbon atoms, chloromethyl, fluoromethyl, carboxyl or hydroxy;
A is —$CH_2$—$CH_2$—, cis—CH=CH—, or trans—CH=CH—;
B is —$CH_2$—$CH_2$— or trans—CH=CH—,
D and E collectively are a direct bond or D is alkylene of 1–5 carbon atoms and E is an oxygen or sulfur atom; esters thereof; readily cleavable 9,15 and 9,15 ethers thereof; methanesulfonylamides thereof, and physiologically acceptable salts thereof with bases; possess the activity of the corresponding natural prostaglandins with a surprisingly longer duration of effectiveness, greater selectivity, and better effects, and can be produced, e.g., by oxidation of the corresponding 9-hydroxy prostaglandins.

18 Claims, No Drawings

NOVEL 11-OXOPROSTAGLANDIN DERIVATIVES

BACKGROUND OF THE INVENTION

This invention relates to novel 11-oxo-prostaglandin acids and derivatives thereof and to processes for their production and use.

Patents which are illustrative of the state of the prior art are U.S. Pat. Nos. 3,639,463; 3,775,462; 3,804,880; 3,816,508; 3,823,180; 3,833,612; 3,836,578; 3,842,118; 3,845,042; 3,847,966; 3,856,852; 3,864,387; and 3,879,423.

It is known that the physiological effects of the prostaglandins in the mammal organism as well as in vitro are only of brief duration, because the prostaglandins are rapidly converted into a plurality of pharmacologically inactive metabolic products. It is also known that the natural prostaglandins per se do not possess any biological specificity, as required from a medicinal agent.

Prostaglandin D₁ (PG D₁)

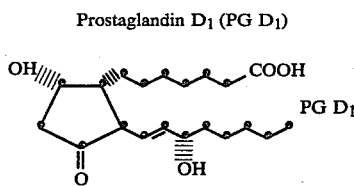

is produced in the biosynthesis in addition to PG E$_1$ and PG F$_{1\alpha}$ from all -cis-8,11,14-eicosa-trienoic acid.

Prostaglandin D₂ (PG D₂)

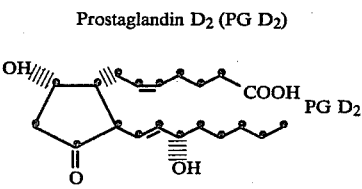

is formed by biosynthesis from arachidonic acids in addition to PG E$_2$ and PG F$_{2\alpha}$.

The natural prostaglandins D$_1$ and D$_2$ exhibit the physiological properties characteristic of the class of prostaglandin compounds, such as, for example, the luteolytic effect, the synchronization of the conception (estrus) cycle in female mammals, and other effects, to a substantially lesser extent (D. H. Nugteren and E. Haselhof, Biochimica et Biophysica Acta, 326 (1973), 448).

It has now been found that 11-oxoprostaglandins of this invention, with structurally modified side chains, possess the activity of the corresponding natural prostaglandins with a surprisingly longer duration of effectiveness, greater selectivity, and better effects.

SUMMARY OF THE INVENTION

In a composition aspect, this invention relates to optically active and racemic 11-oxoprostaglandin derivatives of general Formula I

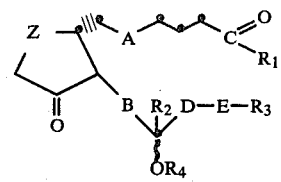

wherein
R$_1$ is —OR$_5$, —NHSO$_2$CH$_3$ or —O—CH$_2$—U—V, R$_5$ being a hydrogen atom, or an alkyl, aryl, or heterocyclic group, U being a direct bond, carbonyl or carbonyloxy, and V being a phenyl ring substituted by one or more of phenyl, alkoxy of 1-2 carbon atoms, and halogen, preferably bromine;
R$_2$ is a hydrogen atom or alkyl of 1-5 carbon atoms;
R$_3$ is alkyl of 1-5 carbon atoms, alkylaryl of up to 10 carbon atoms, cycloalkyl, aryl or benzodioxol-2-yl;
OR$_4$ is a free or etherified hydroxy group, i.e., R$_4$ is a hydrogen atom or the remainder of an ether group;
A is —CH$_2$—CH$_2$—, cis-CH=CH—, or trans-CH=CH—;
B is —CH$_2$—CH$_2$— or trans-CH=CH—;
D and E collectively are a direct bond, or D is straight-chain or branched alkylene of 1-5 carbon atoms and E is an oxygen or sulfur atom; and
Z is >CH~OR$_4$-group, wherein OR$_4$ can be in the α- or β-position and is a free or etherified hydroxy group, i.e., R$_4$ is as defined above;
and, when R$_1$ is hydroxy, physiologically acceptable salts thereof with bases.

In another composition aspect, this invention relates to pharmaceutical compositions comprising a novel 11-oxoprostaglandin of this invention, in unit dosage form, in admixture with a pharmaceutically acceptable carrier.

In process aspects, this invention relates to methods for the production and use of the novel 11-oxo-prostaglandins of this invention.

DETAILED DISCUSSION

Contemplated classes of novel 11-oxoprostaglandins of this invention are:
(a) the free prostanoic acids, i.e., R$_1$ is OH, and physiologically acceptable salts thereof with bases;
(b) the corresponding prostanoic acid esters, i.e., R$_1$ is —O—R$_5$ wherein R$_5$ is a simple, alkyl, aryl or heterocyclic joined to the oxygen atom by a carbon atom thereof;
(c) the corresponding methanesulfonamides, i.e., R$_1$ is —NHSO$_2$CH$_3$;
(d) the corresponding complex prostanoic acid esters, i.e., R$_1$ is —O—CH$_2$—U—V;
(e) each of (a) through (d) wherein —OR$_4$ is a free hydroxy group;
(f) each of (a) through (d) wherein —OR$_4$ is a readily cleaved etherified hydroxy group;
(g) each of (a) through (f) wherein A and B both are —CH$_2$—CH$_2$—;
(h) each of (a) through (f) wherein one of A and B is —CH$_2$—CH$_2$— and the other is —CH=CH$_2$—;
(i) each of (a) through (f) wherein A and B both are —CH=CH$_2$—;
(j) each of (a) through (i) wherein Z is >CHOH;
(k) the readily cleavable ethers of (j).

Preferred classes of 11-oxoprostaglandins of this invention are those wherein:
(1) Z is >CHOH and $R_4$ is H;
(2) at least one of A and B and preferably both is a —CH=CH— group, e.g., (5Z) and (13E)-prostenoic acids and (5Z,13E)-prostadienoic acids, especially those of (1) above;
(3) $R_2$ is a hydrogen atom, D is —$CH_2$—, E is —O— and $R_3$ is aryl, preferably phenyl or substituted phenyl, especially those wherein Z and $R_4$ have the values given in (1) or A and B have the values given in (2), or both;
(4) $R_2$ is a hydrogen atom, D and E collectively are a direct bond and $R_3$ is alkylaryl, preferably phenethyl, especially those wherein Z and $R_4$ have the values given in (1) or A and B have the values given in (2), or both.

The simpliest of the novel 11-oxo-prostaglandin derivatives of this invention are the free hydroxy, free acids, i.e., those of Formula I wherein $R_1$ is OH, Z is >CHOH, and $R_4$ is H. Because activity resides in this unesterified, unetherified moiety, contemplated equivalents thereof are esters thereof, 9, 15, and 9,15 readily cleavable ethers thereof, N-methanesulfonyl-amides thereof, and physiologically acceptable salts thereof with bases.

Preferred esters are alkyl esters of 1–6 carbon atoms, phenylphenylyl esters and phenylphenacyl esters, i.e., $R_1$ is —O—alkyl, —O—$C_6H_4$—$C_6H_5$, or —O—$CH_2CO$—$C_6H_4$—$C_6H_5$. Contemplated equivalents are higher alkyl esters and esters wherein $R_1$ is another —O—$CH_2$—U—V group as defined hereinabove.

The preferred amides are those wherein $R_1$ is —NHSO$_2$CH$_3$.

Preferred 9-,15- and 9,15- ethers are the tetrahydropyranyl, tetrahydrofuranyl and α-ethoxyethyl ethers. Contemplated equivalents are all other readily cleavable ethers.

Examples of $R_1$ ester groups wherein $R_1$ is —O—$CH_2$—U—V are phenyl, 2-,3- or 4-ethoxyphenyl, p-biphenyl, 2-,3- or 4-chloro or -bromophenyl, 2,6-dimethoxyphenyl, 3,5-dibromophenyl, phenacyl, 4-phenylphenacyl and carbophenoxymethyl esters.

Examples of $R_2$ alkyl groups are straight-chain and branched-chain alkyl of 1–5 carbon atoms, such as, for example, the methyl, ethyl, propyl, isopropyl, butyl, isobutyl, and pentyl groups. Methyl and ethyl are preferred.

Examples of substituted and unsubstituted $R_3$ and $R_5$ aryl groups are monocyclic and bicyclic carbocyclic aryl of 6–10 ring carbon atoms, e.g., phenyl, 1-naphthyl, and 2-naphthyl, each of which can be substituted by 1–3 halogen atoms, phenyl, 1–3 alkyl groups, each of 1–4 carbon atoms, chloromethyl, fluoromethyl, trifluoromethyl, carboxyl, or hydroxy.

Examples of $R_5$ and $R_3$ alkyl groups are straight-chain and branched-chain alkyl and the corresponding unsaturated groups, preferably alkyl of 1–10 carbon atoms, especially 1–6 carbon atoms. Examples are methyl, ethyl, propyl, butyl, isobutyl, tert.-butyl, pentyl, hexyl, heptyl, octyl, butenyl, isobutenyl, propenyl, and pentenyl.

Examples of heterocyclic $R_5$ groups are 5- and 6-membered heterocycles attached by a ring carbon atom thereof and having at least one ring hetero atom, preferably nitrogen, oxygen, or sulfur. Examples are 2-furyl, 2-thienyl, 2-pyridyl and 3-pyridyl.

Examples of cycloalkyl $R_3$ groups are those containing 4–10 carbon ring atoms, preferably 5 or 6. The rings can be substituted, e.g., by alkyl of 1–4 carbon atoms. Examples are cyclopentyl, cyclohexyl, methylcyclohexyl, and adamantyl.

Examples of suitable $R_4$ ether residues are tetrahydropyranyl, tetrahydrofuranyl and α-ethoxyethyl. Others are those known to be readily cleavable.

For salt formation, inorganic and organic bases conventionally employed for the production of physiologically acceptable salts can be used. Examples are the alkali hydroxides, e.g., sodium and potassium hydroxide, the alkaline earth hydroxides, e.g., calcium hydroxide, ammonia, and amines, e.g., ethanolamine, diethanolamine, triethanolamine, N-methylglucamine, morpholine and tris(hydroxymethyl)-methylamine.

In a process aspect, this invention relates to a process for the preparation of the novel 11-oxoprostaglandin derivatives of Formula I by conventionally oxidizing compounds of Formula II

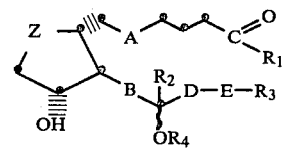

wherein $R_1$, $R_2$, $R_3$, $R_4$, A, B, D, E, and Z have the values given above, and optionally thereafter, in any desired sequence, esterifying a free carboxy group and/or hydrogenating a 5,6-double bond and/or hydrogenating a 13,14- and a 5,6-double bond and/or functionally modifying a free OH-group and/or liberating a functionally modified OH-group and converting a 1-carboxy compound with a base into a physiologically compatible salt and optionally separating the racemates.

The oxidation of the 11-hydroxy group is effected in accordance with methods know to persons skilled in the art. Examples of suitable oxidizing agents are: Jones reagent (J. Chem. Soc. 1953, 2555), Collins reagent (Tetrahedron Letters, 1968, 3368), Fetizon reagent (Tetrahedron 29, 2867 [1973]), platinum with oxygen (Adv. in Carbohydrate Chem. 17, 169 [1962]), or silver carbonate. For example, the oxidation with Jones reagent or Collins reagent results, starting with 9α-hydroxy compounds, regioselectively in very good yields of 11-oxoprostaglandin derivatives. The oxidation is conducted with Jones reagent at −40° to +20° C., preferably at −30° to −10° C. or, with Collins reagent, at −20° to +30° C., preferably at 0° to 20° C., in a solvent inert with respect to the oxidizing agent. Suitable solvents are methylene chloride, chloroform, ethylene chloride, pyridine, and others, but preferably methylene chloride.

The oxidation with Fetizon reagent, silver carbonate, or platinum with oxygen, for example, yields starting with 9β-hydroxy compounds, 11-oxoprostaglandin derivatives. Suitable solvents are benzene, toluene, xylene, ethyl acetate, acetone, tetrahydrofuran, diethyl ethers, and dioxane, and other inert solvents. The reaction temperatures range between 20° C. and 110° C. in the silver carbonate or Fetizon oxidation, preferably being the boiling temperature of the solvent. During the oxidation of platinum/oxygen, temperatures are utilized of preferably 20°–50° C.

The liberation of the functionally modified hydroxy group to obtain the compounds of general Formula I takes place according to known methods. For example, the cleavage of ether blocking groups is accomplished in an aqueous solution of an organic acid, such as, for example, acetic acid, propionic acid, etc., or in an aqueous solution of an inorganic acid, such as hydrochloric acid. To improve the solubility, a water-miscible inert organic solvent is suitably added. Advantageous organic solvents in this connection are, for instance: alcohols, such as methanol and ethanol, and ethers, such as dimethoxyethane, dioxane, and tetrahydrofuran. Tetrahydrofuran is preferred. The splitting off reaction is preferably accomplished at temperatures of between 20° and 80° C.

The functional modification of the free OH-groups takes place according to methods known to those skilled in the art. For example, the reaction is carried out with dihydropyran in methylene chloride or chloroform with the use of an acidic condensation agent, such as p-toluenesulfonic acid, for example. The dihydropyran is used in excess, preferably in 4–10 times the theoretically required quantity. The reaction is normally finished at 0°–30° C. after 15–30 minutes.

The introduction of the ester group —OR$_5$ for R$_1$, wherein R$_5$ is an alkyl group of 1–10 carbon atoms, takes place according to methods known to persons skilled in the art. The 1-carboxy compounds are reacted, for example, with diazohydrocarbons in a conventional manner. The esterification with diazohydrocarbons is effected, for example, by combining a solution of the diazohydrocarbon in an inert solvent, preferably in diethyl ether, with the 1-carboxy compound in the same or another inert solvent, such as, for example, methylene chloride. After the reaction is terminated within 1–30 minutes, the solvent is removed and the ester purified in the usual way.

Diazoalkanes are either known or can be prepared in accordance with conventional methods [Org. Reactions 8, 389–394 (1954)].

The ester group —OR$_5$ is introduced for R$_1$, wherein R$_5$ is a substituted or unsubstituted aryl group, in accordance with methods known to a person skilled in the art. For example, the 1-carboxy compounds are reacted with the corresponding arylhydroxy compounds with dicyclohexylcarbodiimide in the presence of a suitable base, e.g. pyridine or triethylamine, in an inert solvent. Suitable solvents are methylene chloride, ethylene chloride, chloroform, ethyl acetate, tetrahydrofuran, preferably chloroform. The reaction is conducted at temperatures of between −30° and +50° C., preferably at 10° C.

In order to introduce the ester group O—CH$_2$—U—V for R$_1$, the 1-carboxy compound of general Formula I is reacted, in the presence of an agent splitting off hydrogen halide, with a halogen compound of the general formula

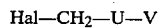
Hal—CH$_2$—U—V wherein
Hal is a halogen atom, preferably bromine,
U is a direct bond, carbonyl or carbonyloxy, and
V is a phenyl ring substituted by one or more phenyl groups, alkoxy groups of 1–2 carbon atoms, or halogen atoms, preferably bromine atoms.

Examples of agents which split off hydrogen halide are silver oxide, sodium carbonate, potassium carbonate, sodium bicarbonate, potassium bicarbonate, or amines, such as trimethylamine, triethylamine, tributylamine, trioctylamine, and pyridine. The reaction with the halogen compound is conducted in an inert solvent, preferably in acetone, acetonitrile, dimethylacetamide, dimethylformamide, or dimethyl sulfoxide at temperatures of −80° to +100° C., preferably at room temperature.

The hydrogenation of the 13,14- and 5,6-double bonds takes place conventionally in a hydrogen atmosphere in the presence of a noble metal catalyst. A suitable catalyst is, for example, 10% palladium on charcoal. If the hydrogenation is carried out at room temperature, it is possible to saturate the 5,6-double bond as well as the 13,14-double bond.

At low temperatures, preferably at −80° to −10° C., the cis-5,6-double bond can be hydrogenated before the trans-13,14-double bond. A selective reduction of the cis-5,6-double bond with the simultaneous presence of a trans-13,14-double bond is also effected with the use of the catalyst tris(triphenylphosphine)rhodium(I) chloride at temperatures of between 0° and 40° C., preferably at 20° to 30° C.

The prostaglandin derivatives of general Formula I wherein R$_1$ is a hydroxy group can be converted into salts with suitable amounts of the corresponding inorganic bases under neutralization. For example, when dissolving the corresponding PG acids in water containing the stoichiometric quantity of the base, the solid inorganic salt is obtained after evaporation of the water or after the addition of a water-miscible solvent, e.g., alcohol or acetone.

To prepare an amine salt, which process is conducted in the usual manner, the PG acid is dissolved, for example, in a suitable solvent, e.g., ethanol, acetone, diethyl ether, or benzene, and at least the stoichiometric amount of the amine is added to this solution. During this step, the salt is ordinarily obtained in the solid form or is isolated after evaporation of the solvent in the usual manner.

The racemates are separated in accordance with conventional methods, such as by salt formation with an optically active base, e.g. dihydroabietylamine, amphetamine, quinine, and others.

The compounds of general Formula II serving as the starting materials can be prepared by conventionally reducing a ketone of general Formula III

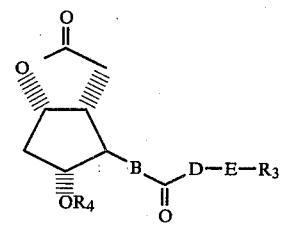

wherein R$_3$, R$_4$, E, D, and B have the values given above, with, for example, zinc borohydride, to the epimeric 15α- and 15β-alcohol (PG numbering). Optionally, the epimeric alcohols can be separated. The R$_2$ group can be introduced according to the customary methods, for example by reacting the ketone of general Formula III with alkyl magnesium bromide and alkyl lithium. After the introduction of a hydroxy blocking group on the C-15 atom, such as for example with dihydropyran, the lactone is reduced to the lactol with diisobutyl aluminum hydride. The reaction with a Wittig reagent leads to the 9α-hydroxy compounds of general Formula II.

If $R_1$ represents an ester group in compounds of general Formula II, the saponification of the prostaglandin esters can be conducted according to methods known to those skilled in the art, such as, for example, with basic catalysts or by reductive cleavage.

To produce the 9β-hydroxy compounds of Formula II, the 9α-hydroxy group is oxidized regioselectively to the ketone. The subsequent reduction with, for example, sodium borohydride or zinc borohydride leads to a mixture of epimers which can be separated according to conventional methods.

The novel 11-oxoprostanoic acid derivatives of general Formula I are valuable pharmaceuticals, since they exhibit with a similar activity spectrum an essentially stronger and particularly substantially longer effectiveness than the corresponding natural prostaglandins, such as, for example PG $E_2$, $F_{2\alpha}$, and $D_2$.

The novel prostaglandin analogs of the D-type have a very strong luteolytic effect, i.e., for triggering luteolysis, substantially lower dosages are required than in case of the corresponding natural prostaglandins, such as PG $F_{2\alpha}$, for example.

Also for the triggering of abortions, substantially lower quantities of the novel prostaglandin analogs are required as compared to the natural prostaglandins.

When registering the isotonic uterus contraction on narcotized rats and on the isolated rat uterus, it is found that the compounds of this invention are substantially more effective and of a longer duration of activity than the natural prostaglandins.

The novel prostanoic acid derivatives are suitable, after a one-time intrauterine administration, to induce menstruation or to interrupt a pregnancy. They are furthermore advantageous for synchronizing the conception cycle in female mammals, such as monkeys, rabbits, cattle, pigs, etc.

The good dissociation of effectiveness of the novel compounds of this invention can be observed when testing these compounds on other smooth muscle organs, such as, for example, on the guinea pig ileum or on the isolated rabbit trachea, where a substantially lower effectiveness can be observed than that caused by the natural prostaglandins.

The effective agents of this invention have a regulating effect in cardiac dysrhythmia; they lower the blood pressure, have a diuretic activity, and inhibit thrombocyte aggregation.

The novel compounds of this invention have a lesser bronchoconstrictive effect than natural prostaglandin $F_{2\alpha}$, which is of great advantage for their therapeutic application. For medical purposes, the active agents can be converted into a form suitable for oral or parenteral application.

For oral administration, for example, tablets, dragees, or capsules are suitable.

For parenteral application, sterile aqueous or oily solutions amenable to injection are utilized.

Accordingly, this invention also relates to medicinal agents on the basis of the compounds of general Formula I and customary auxiliary agents and carriers.

The effective agents of this invention are to serve, in conjunction with the auxiliary agents known and customary in galenic pharmacy, for example to produce preparations for triggering abortion, for cycle control, or for the induction of labor. For this purpose, sterile aqueous solutions containing 0.01–10 μg./ml. of the active compound can be utilized as an intravenous infusion. To produce aqueous isotonic solutions, the acids and salts of general Formula I are especially suitable. To increase solubility, it is possible to add alcohols, such as ethanol and ethylene glycol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The temperatures in the examples are set forth in degrees Celsius.

EXAMPLE 1

(5Z,13E)-(8R,9S,12R,15S)-9,15-Dihydroxy-11-oxo-16-phenoxy-17,18,19,20-tetranor-prostadienoic Acid At −20°, 0.14 ml. of Jones reagent (J. Chem. Soc. 1953, 2555) was added to a solution of 200 mg. of (5Z,13E)-(8R,9S,11R,12R,15S)-9,11-dihydroxy-16-phenoxy-15-(tetrahydropyran-2-yloxy)-17,18,19,20-tetranor-prostadienoic acid in 4 ml. of acetone. The mixture was stirred for 25 minutes at −20°, the excess reagent was destroyed by the dropwise addition of 0.25 ml. of isopropanol, the mixture was combined with 50 ml. of water and extracted three times with respectively 50 ml. of ether. The organic extract was shaken three times with respectively 30 ml. of brine, dried over magnesium sulfate, and evaporated under vacuum. After chromatographing the crude product on silica gel, 120 mg. of (5Z,13E)-(8R,9S,12R,15S)-9-hydroxy-11-oxo-16-phenoxy-15-(tetrahydropyran-2-yloxy)-17,18,19,20-tetranor-prostadienoic acid is obtained with ethyl acetate/hexane (1+1) as a colorless oil.

To split off the blocking group, the 11-ketone produced in this way was agitated with 4 ml. of a mixture of acetic acid/water/tetrahydrofuran (65/35/10) for 5 hours at 38°. After evaporation under vacuum and chromatography on silica gel with chloroform/isopropanol (9+1), 65 mg. of the title compound was obtained as a colorless oil.

For purposes of conducting the thin-layer chromatography (TLC), silica gel plates were utilized (Merck, 0.25 mm. layer thickness).

TLC (chloroform/tetrahydrofuran/glacial acetic acid 20/4/2): Rf value 0.41.

The IR spectra were in all cases taken in chloroform solution.

IR: 3600, 3460 (wide), 2998, 2930, 2860, 1740, 1710, 1600, 1588, 1497, 972 cm$^{-1}$.

The starting material for the above title compound was prepared as follows:

1(a)

(1S,5R,6R,7R,3'S)-6[(E)-3-(Tetrahydropyran-2-yloxy)-4-phenoxy-1-butenyl]-7-benzoyloxy-2-oxabicyclo[3,3,0]octan-3-one A mixture of 2.06 g. of (1S,5R,6R,7R,3'S)-6-[(E)-3-hydroxy-4-phenoxy-1-butenyl]-7-benzoyloxy-2-oxabicyclo[3,3,0]-octan-3-one (see DOS [German Unexamined Laid-Open Application] No. (2,322,673), 2.2 ml. of dihydropyran, and 20 mg. of p-toluenesulfonic acid was stirred in 60 ml. of dried methylene chloride for 30 minutes at 5° under argon. After dilution with methylene chloride, the mixture was shaken with saturated sodium bicarbonate solution and water, dried over magnesium sulfate, and evaporated under vacuum. After filtering the residue over a small amount of silica gel, 2.21 g. of the title compound was obtained with ether/hexane (7+3) was a colorless oil.

TLC (ether): Rf value 0.56.

IR: 2998, 2950, 1765, 1715, 1600, 1588, 1497, 972 cm$^{-1}$.

1(b)
(2RS,3aR,4R,5R,6aS,3′S)-4-[(E)-3-(Tetrahydropyran-2-yloxy)-4-phenoxy-1-butenyl]-perhydrocyclopenta[b]furan-2,5-diol Under argon, 20 ml. of a 20% solution of diisobutyl aluminum hydride in toluene was added to a solution, cooled to −60°, of 2.97 g. of the compound prepared according to Example 1(a) in 100 ml. of dry toluene. The mixture was stirred for 30 minutes at −60° and the reaction was then terminated by the dropwise addition of isopropanol. The mixture was combined with 10 ml. of water, allowed to warm up to room temperature, stirred for 30 minutes, filtered, and the solution was evaporated under vacuum. After filtration over silica gel with ether, 2.01 g. of the title compound was obtained as a colorless oil.

TLC (ether): Rf value 0.25.

IR: 3600, 2998, 2950, 1600, 1588, 1497, 975 cm$^{-1}$.

1(c)
(5Z,13E)-(8R,9S,11R,12R,15S)-9,11-Dihydroxy-16-phenoxy-15-(tetrahydropyran-2-yloxy)-17,18,19,20-tetranor-prostadienoic Acid At 15°, 50 ml. of a solution of methanesulfinylmethylsodium in dry DMSO (prepared by dissolving 2.5 g. of 50% sodium hydride suspension in 50 ml. of dry DMSO during the course of one hour at 75°) was added dropwise to a solution of 11.5 g. of 4-carboxybutyltriphenylphosphonium bromide in 50 ml. of dry dimethyl sulfoxide (DMSO). The mixture was stirred for 30 minutes at room temperature. A solution of 2.01 g. of the lactol obtained according to Example 1(b) in 25 ml. of DMSO was added to the red ylene solution, and the mixture was agitated for 2.5 hours at 45°. After the solvent had been extensively distilled off under vacuum, the mixture was combined with 80 ml. of water, shaken three times with respectively 100 ml. of ether, and the ether extract was discarded. The aqueous phase was acidified with 10% citric acid solution to pH 4–5 and extracted four times with respectively 150 ml. of a mixture of ether/pentane (2+1). The organic phase was shaken with brine, dried over magnesium sulfate, and evaporated under vacuum. After chromatography of the residue on silica gel, 1.20 g. of the title compound was obtained with chloroform/isopropanol (8+2) as a colorless oil.

TLC (chloroform/methanol 85+15): Rf value 0.70

IR: 3600, 3460 (wide), 2998, 2950, 1710, 1600, 1588, 1496, 975 cm$^{-1}$.

EXAMPLE 2
(5Z,13E)-(8R,9S,12R,15S)-9,15-Dihydroxy-11-oxo-17-phenyl-18,19,20-trinor-prostadienoic Acid 900 mg. of (5Z,13E)-(8R,9S,11R,12R,15S)-9,11-dihydroxy-17-phenyl-15-(tetrahydropyranyloxy)-18,19,20-trinorprostadienoic acid was converted into the 11-keto compound analogously to Example 1 and then the blocking group was removed, thus obtaining 390 mg. of the title compound as a colorless oil.

TLC (chloroform/tetrahydrofuran/glacial acetic acid 20/4/2): Rf value 0.45.

IR: 3595, 3300 (wide), 3000, 2950, 2860, 1740, 1710, 1602, 1495, 970 cm$^{-1}$.

NMR (DMSO-d$_6$) δ: 7.05–7.25 (5H,m); 5.27–5.68 (4H,m); 4.86 J=4 Hz (1H,d); 4.71 J=4.5 Hz (1H,d); 4.22 (1H,m); 3.8–4.0 (1H,m).

The starting material for the above title compound was prepared as follows:

2(a)
(1S,5R,6R,7R)-6-[(E)-3-Oxo-5-phenyl-1-pentenyl]-7-benzoyloxy-2-oxabicyclo[3,3,0]octan-3-one At 20° under argon, 20 ml. of a 2-molar butyllithium solution in hexane was added dropwise to a solution of 11.2 g. of dimethyl-2-oxo-4-phenylbutylphosphonate in 400 ml. of ether. The mixture was stirred for 5 minutes and then 600 ml. of ether was added thereto and the mixture again stirred for 5 minutes at 20°. Thereafter, a solution of 9.26 g. of (1S,5R,6R,7R)-6-formyl-7-benzoyloxy-2-oxabicyclo[3,3,0]octan-3-one [J. Amer. Chem. Soc. 96, 5865 (1974)] in 150 ml. of tetrahydrofuran was added dropwise to this mixture, and the latter was agitated for 30 minutes at 20°. 6 ml. of glacial acetic acid was added thereto, and the mixture was evaporated under vacuum. The residue was taken up in 600 ml. of methylene chloride, shaken twice with respectively 100 ml. of saturated sodium bicarbonate solution, twice with respectively 100 ml. of water, dried over magnesium sulfate, and evaporated under vacuum. After recrystallization from isopropyl ether/methylene chloride, 11 g. of the title compound was obtained as colorless crystals; m.p. 119°–120°.

2(b)
(1S,5R,6R,7R,3′S)-6-[(E)-3-Hydroxy-5-phenyl-1-pentenyl]-7-benzoyloxy-2-oxabicyclo[3,3,0]octan-3-one A solution of 10 g. of the ketone obtained according to Example 2(a) in 500 ml. of dimethoxyethane was combined dropwise at room temperature with 500 ml. of ethereal zinc borohydride solution (preparation see "Neuere Methoden der praeparativen organischen Chemie" [More Recent Methods of Preparative Organic Chemistry], 4, 241, publishers: Chemie], and the mixture was agitated for 2 hours at room temperature. Thereafter, the mixture was combined dropwise with 50 ml. of water, agitated for 30 minutes at room temperature, filtered, the filtrate was dried over magnesium sulfate, and evaporated under vacuum. After chromatographing the residue from the evaporation on silica gel with ether/hexane (8+2), 4.60 g. of the title compound was obtained first of all as colorless crystals, m.p. 86°–87°, and then, as the more polar component, 3.1 g. of the epimer was produced, namely (1S,5R,6R,7R,3′R)-6-[(E)-3-hydroxy-5-phenyl-1-pentenyl]-7-benzoyloxy-2-oxabicyclo[3,3,0]octan-3-one as a colorless oil.

TLC (ether):
3′S epimer Rf value 0.28
3′R epimer Rf value 0.24

2(c)
(1S,5R,6R,7R,3′S)-6-[(E)-3-(Tetrahydropyran-2-yloxy)-5-phenyl-1-pentenyl]-7-benzoyloxy-2-oxabicyclo[3,3,0]octan-3-one A mixture of 4.5 g. of the alcohol prepared according to Example 2(b), 3.5 ml. of dihydropyran, and 35 mg. of p-toluenesulfonic acid was agitated in 100 ml. of dry methylene chloride for 30 minutes at 0° under argon.

After dilution with methylene chloride, the mixture was shaken with saturated sodium bicarbonate solution and water, dried over magnesium sulfate, and evaporated under vacuum. After filtering the residue over silica gel, ether/hexane (7+3), 5.2 g. of the title compound was obtained as a colorless oil.

TLC (ether): Rf value 0.57.

IR: 2998, 2950, 1765, 1715, 1600, 1495, 975 cm$^{-1}$.

2(d)
(2RS,3aR,4R,5R,6aS,3'S)-4-[(E)-3-Tetrahydropyran-2-yloxy)-5-phenyl-1-pentenyl]-perhydrocyclopenta[b]furan-2,5-diol Under argon, 50 ml. of a 20% solution of diisobutyl aluminum hydride in toluene was added to a solution of 5 g. of the compound prepared according to Example 2(c) in 250 ml. of toluene, cooled to −60°. The mixture was stirred for 30 minutes at −70° and the reaction was then terminated by the dropwise addition of isopropanol. The mixture was then combined with 25 ml. of water, allowed to warm up to room temperature, stirred for 30 minutes, filtered, and the solution evaporated under vacuum. After filtration over silica gel with ether, 3.6 g. of the title compound was obtained in the form of colorless crystals, m.p. 101°-103°.

2(e)
(5Z,13E)-(8R,9S,11R,12R,15S)-9,11-Dihydroxy-15-(tetrahydropyran-2-yloxy)-17-phenyl-18,19,20-trinor-prostadienoic Acid At 15°, 75.3 ml. of a solution of methanesulfinylmethylsodium in dry DMSO (prepared by dissolving 3.6 g. of 50% sodium hydride suspension in 75 ml. of DMSO during the course of one hour at 75° and stirring the mixture at room temperature for 30 minutes under argon) was added dropwise to a solution of 18.3 g. of 4-carboxybutyltriphenylphosphonium bromide in 80 ml. of DMSO. The mixture was agitated for 30 minutes at room temperature. Thereafter, a solution of 3.2 g. of the lactol obtained according to Example 2(d) in 50 ml. of absolute DMSO was added dropwise to the red ylene solution, and the mixture was stirred for 2 hours at 50° under argon. Then, the mixture was combined with 150 ml. of water, shaken three times with respectively 100 ml. of ether, and the ether extract was discarded. The aqueous phase was acidified to pH 4-5 with 10% citric acid solution and extracted four times with respectively 200 ml. of a mixture of ether/pentane (2+1). The organic extract was shaken with brine, dried over magnesium sulfate, and evaporated under vacuum. After chromatography of the residue on silica gel, 2.90 g. of the title compound was obtained with chloroform/isopropanol (8+2) as a colorless oil.

TLC (chloroform/methanol 85+15): Rf value 0.70.

IR: 3600, 3460 (wide), 2999, 2950, 1710, 1600, 1495, 975 cm$^{-1}$.

NMR (DMSO-d$_6$) δ: 7.15 (5H,m); 5.1-5.5 (4H,m); 4.61 (1H,m); 3.6-4.0 (2H,m).

EXAMPLE 3
(5Z,13E)-(8R,9S,12R,15R)-9,15-Dihydroxy-11-oxo-16-phenoxy-17,18,19,20-tetranor-prostadienoic Acid In analogy to Example 1, starting with (1S,5R,6R,7R,-3'R)-6-[(E)-3-hydroxy-4-phenoxy-1-butenyl]-7-benzoyloxy-2-oxabicyclo[3,3,0]octan-3-one (see DOS No. 2,322,673), the title compound was obtained as a colorless oil.

TLC (chloroform/tetrahydrofuran/glacial acetic acid 20/4/2): Rf value 0.46.

IR: 3600, 3460 (wide), 2998, 2930, 2860, 1740, 1710, 1600, 1588, 1498, 974 cm$^{-1}$.

EXAMPLE 4
(5Z,13E)-(8R,9S,12R,15R)-9,15-Dihydroxy-11-oxo-17-phenyl-18,19,20-trinor-prostadienoic Acid Analogously to Example 2, the title compound was obtained as a colorless oil, starting with the (3'R)-configured compound obtained according to Example 2(b).

TLC (chloroform/tetrahydrofuran/glacial acetic acid 20/4/2): Rf value 0.49.

IR: 3595, 3300 (wide), 3000, 2950, 2860, 1740, 1710, 1602, 1495, 970 cm$^{-1}$.

EXAMPLE 5
(5Z)-(8R,9S,12R,15S)-9,15-Dihydroxy-11-oxo-16-phenoxy-17,18,19,20-tetranor-prostenoic Acid 500 mg. of (5Z)-(8R,9S,11R,12R,15S)-9,11-dihydroxy-16-phenoxy-15-(tetrahydropyran-2-yloxy)-17,18,19,20-tetranor prostenoic acid was converted analogously to Example 1 into the 11-keto compound and then the blocking group was removed, thus obtaining 210 mg. of the title compound as a colorless oil.

TLC (chloroform/tetrahydrofuran/glacial acetic acid 20/4/2): Rf value 0.42.

IR: 3600, 3460 (wide), 2998, 2935, 2860, 1740, 1710, 1600, 1588, 1497 cm$^{-1}$.

The starting material was produced as follows:

5(a)
(1S,5R,6R,7R,3'S)-6-[3-(Tetrahydropyran-2-yloxy)-4-phenoxy-1-butyl]-7-benzoyloxy-2-oxabicyclo[3,3,0]octan-3-one A solution of 2 g. of the compound prepared according to Example 1(a) in 100 ml. of ethyl acetate was shaken with 200 mg. of palladium (10% on charcoal) for 2 hours under a hydrogen atmosphere at room temperature. The mixture was then filtered and evaporated under vacuum, thus obtaining 1.98 g. of the title compound as a colorless oil.

TLC (ether): Rf value 0.58.

IR: 2998, 2950, 1765, 1715, 1600, 1588, 1497 cm$^{-1}$.

The NMR spectrum (in CDCl$_3$) did not show any olefinic protons.

5(b)
(2RS,3aR,4R,5R,6aS,3'S)-4-[3-(Tetrahydropyran-2-yloxy)-4-phenoxy-1-butyl]-perhydrocyclopenta[b]furan-2,5-diol Analogously to Example 1(b), 1.38 g of the title compound was obtained as a colorless oil from 1.92 g. of the compound prepared according to Example 5(a).

TLC (ether): Rf value 0.27.

5(c)
(5Z)-(8R,9S,11R,12R,15S)-9,11-Dihydroxy-16-phenoxy-15-tetrahydropyran-2-yloxy-17,18,19,20-tetranor-prostenoic Acid In analogy to Example 1(c), 0.63 g. of the title compound was formed as a colorless oil from 1.2 g. of the compound prepared according to Example 5(b).

TLC (chloroform/methanol 85+15): Rf value 0.71.

IR: 3600, 3450 (wide), 2998, 2950, 1710, 1600, 1588, 1496 cm$^{-1}$.

EXAMPLE 6

(5Z,13E)-(8R,9S,12R,15S)-9,15-Dihydroxy-11-oxo-16-(4-chlorophenoxy)-17,18,19,20-tetranor-prostadienoic Acid By proceeding in accordance with Example 2, but with the use of dimethyl-[2-oxo-3-(p-chlorophenoxy)-propyl]-phosphonate (DOS's No. 2,322,673 and 2,223,365), the title compound was obtained as a colorless oil.

TLC (chloroform/tetrahydrofuran/glacial acetic acid 20/4/2): Rf value 0.46.

IR: 3600, 3450 (wide), 2998, 2965, 2890, 1740, 1710, 1597, 1582, 1490 (strong), 978, 872, 823 cm$^{-1}$.

EXAMPLE 7

(5Z,13E)-(8R,9S,12R,15S)-9,15-Dihydroxy-11-oxo-16-(3-trifluoromethylphenoxy)-17,18,19,20-tetranor-prostadienoic Acid By proceeding analogously to Example 2, but with the use of dimethyl-[2-oxo-3-(3-trifluoromethylphenoxy)-propyl]-phosphonate (DOS's No. 2,322,673 and 2,223,365), the title compound is produced as a colorless oil.

TLC (chloroform/tetrahydrofuran/glacial acetic acid 20/4/2): Rf value 0.48.

IR: 3600, 3460 (wide), 2998, 2965, 2890, 1740, 1710, 1584, 1490, 1450, 975 cm$^{-1}$.

EXAMPLE 8

(5Z,13E)-(8R,9S,12R,15S)-9,15-Dihydroxy-11-oxo-16-(4-fluorophenoxy)-17,18,19,20-tetranor-prostadienoic Acid Following the method of Example 2, but using dimethyl-[2-oxo-3-(4-fluorophenoxy)-propyl]-phosphonate (DOS's No. 2,322,673 and 2,223,365), the title compound is the result in the form of a colorless oil.

TLC (chloroform/tetrahydrofuran/glacial acetic acid 20/4/2): Rf value 0.44.

IR: 3600, 3450 (wide), 2998, 2960, 2860, 1740, 1710, 1600, 1500, 1450, 978, 830 cm$^{-1}$.

EXAMPLE 9

(5Z,13E)-(8R,9S,12R,15S)-9,15-Dihydroxy-11-oxo-16-(3-chlorophenoxy)-17,18,19,20-tetranor-prostadienoic Acid By proceeding in accordance with Example 2, but with the utilization of dimethyl-[2-oxo-3-(3-chlorophenoxy)-propyl]-phosphonate (DOS's No. 2,322,673 and 2,223,365), the title compound is produced as a colorless oil.

TLC (chloroform/tetrahydrofuran/glacial acetic acid 20/4/2): Rf value 0.43.

IR: 3600, 3460 (wide), 2998, 2960, 2860, 1740, 1710, 1600, 975 cm$^{-1}$.

EXAMPLE 10

(5Z,13E)-(8R,9S,12R,15R)-9,15-Dihydroxy-11-oxo-15-(4-chlorophenyl)-16,17,18,19,20-pentanor-prostadienoic Acid Following Example 2, but using dimethyl-[2-oxo-2-(4-chlorophenyl)-ethyl]-phosphonate (see DOS No. 2,322,142), the title compound is obtained as a colorless oil.

TLC (chloroform/tetrahydrofuran/glacial acetic acid 20/4/2): Rf value 0.43.

IR: 3600, 3450 (wide), 3000, 2960, 2860, 1740, 1710, 1598, 1488, 970, 872 cm=$^{1}$.

EXAMPLE 11

By proceeding analogously to Examples 2 and 5, using the corresponding phosphonates described in the laid-open applications which follow: (DOS's No. 2,322,673; 2,223,365; 2,234,709; 2,234,708; 2,322,142), the following novel 11-oxo-prostaglandin acids are obtained:

(5Z)-(8R,9S,12R,15R)-9,15-dihydroxy-11-oxo-16-phenoxy-17,18,19,20-tetranor-prostenoic acid (5Z,13E)-(8R,9S,12R,15R)-9,11-dihydroxy-11-oxo-16-(4-chlorophenoxy)-17,18,19,20-tetranor-prostadienoic acid (5Z,13E)-(8R,9S,12R,15R)-9,15-dihydroxy-11-oxo-16-(3-trifluoromethylphenoxy)-17,18,19,20-tetranor-prostadienoic acid (5Z,13E)-(8R,9S,12R,15R)-9,15-dihydroxy-11-oxo-16-(4-fluorophenoxy)-17,18,19,20-tetranor-prostadienoic acid (5Z,13E)-(8R,9S,12R,15R)-9,15-dihydroxy-11-oxo-16-(3-chlorophenoxy)-17,18,19,20-tetranor-prostadienoic acid (5Z,13E)-(8R,9S,12R,15R)-9,15-dihydroxy-11-oxo-15-(4-chlorophenyl)-16,17,18,19,20-pentanor-prostadienoic acid (5Z,13E)-(8R,9S,12R,15S)-9,15-dihydroxy-11-oxo-16-(3-fluorophenoxy)-17,18,19,20-tetranor-prostadienoic acid (5Z,13E)-(8R,9S,12R,15R)-9,15-dihydroxy-11-oxo-16-(3-fluorophenoxy)-17,18,19,20-tetranor-prostadienoic acid (5Z,13E)-(8R,9S,12R,15S)-9,15-dihydroxy-11-oxo-17-(4-fluorophenyl)-18,19,20-trinor-prostadienoic acid (5Z,13E)-(8R,9S,12R,15R)-9,15-dihydroxy-11-oxo-17-(4-fluorophenyl)-18,19,20-trinor-prostadienoic acid.

EXAMPLE 12

(5Z,13E)-(8R,9R,12R,15S)-9,15-Dihydroxy-11-oxo-16-phenoxy-17,18,19,20-tetranor-prostadienoic Acid Under a hydrogen atmosphere, 2 g. of platinum dioxide was agitated for one hour in 20 ml. of ethyl acetate; the mixture was purged with nitrogen and then agitated for 4 hours under oxygen. To this mixture was added a solution of 200 mg. of (5Z,13E)-(8R,9R,11R,12R,15S)-9,11-dihydroxy-16-phenoxy-15-tetrahydropyran-2-yloxy)-17,18,19,20-tetranor-prostadienoic acid in 10 ml. of ethyl acetate; and this mixture was stirred for 18 hours under oxygen at room temperature, then filtered, and the residue from the evaporation was chromatographed on silica gel. With methylene chloride/isopropanol (9+1), 60 mg. of the 11-oxo compound was produced in addition to the 9-oxo compound; this 11-oxo compound was then agitated with 4 ml. of a mixture of acetic acid/water/tetrahydrofuran (65/35/10) for 5 hours at 38°. After evaporation and chromatography on silica gel with chloroform/isopropanol (8+2), 37 mg. of the title compound was obtained as a colorless oil.

TLC (chloroform/tetrahydrofuran/glacial acetic acid 20/4/2): Rf value 0.34.

IR: 3600, 3460 (wide), 2998, 2930, 2860, 1740, 1710, 1600, 1588, 1498, 975 cm$^{-1}$.

The starting material for the above title compound was produced as follows:

12(a)

(5Z,13E)-(8R,11R,12R,15S)-11-Hydroxy-9-oxo-16-phenoxy-15-(tetrahydropyran-2-yloxy)-17,18,19,20-tetranor-prostadienoic Acid Under a hydrogen atmosphere, 4 g. of platinum dioxide was agitated in 40 ml. of ethyl acetate for 1 hour. The mixture was purged with nitrogen and then stirred for 4 hours under an oxygen atmosphere. To this mixture was added a solution of 400 mg. of the compound prepared according to Example 1(c) in 15 ml. of ethyl acetate and agitated for 15 hours under oxygen at room temperature. The mixture was then filtered. Chromatography of the evaporation residue on silica gel with methylene chloride/isopropanol (9+1) yielded 295 mg. of the title compound as a colorless oil.

TLC (methylene chloride/isopropanol 9+1): Rf value 0.48.

12(b)

(5Z,13E)-(8R,9R,11R,12R,15S)-9,11-Dihydroxy-16-phenoxy-15-(tetrahydropyran-2-yloxy)-17,18,19,20-tetranor-prostadienoic Acid A solution of 1 g. of sodium borohydride in 150 ml. of methanol was added dropwise at ice bath temperature to a solution of 500 mg. of the compound prepared according to Example 12(a) in 40 ml. of methanol. The mixture was stirred for 20 minutes at ice bath temperature, for 20 minutes at room temperature, and then concentrated under vacuum. After dilution with 60 ml. of water, a pH of 4 was set with 10% citric acid solution, and the mixture was extracted three times with respectively 80 ml. of methylene chloride, the organic extract was shaken twice with respectively 30 ml. of brine, dried over magnesium sulfate, and evaporated under vacuum. After chromatography of the evaporation residue on silica gel, 230 mg. of the title compound was obtained with chloroform/isopropanol (8+2) as a colorless oil.

TLC (chloroform/methanol 85+15): Rf value 0.58.
IR: 3600, 3460 (wide), 2998, 2950, 1710, 1600, 1588, 1497, 976 cm$^{-1}$.

EXAMPLE 13

(8R,9S,12R,15S)-9,15-Dihydroxy-11-oxo-16-phenoxy-17,18,19,20-tetranor-prostanoic Acid A solution of 250 mg. of the compound obtained according to Example 1 was shaken in 20 ml. of ethyl acetate with 25 mg. of palladium (10% on charcoal) for 1 hour at room temperature under a hydrogen atmosphere. After filtration, chromatography of the evaporation residue on silica gel with chloroform/isopropanol (9+1) yielded 160 mg. of the title compound as a colorless oil.

TLC (chloroform/tetrahydrofuran/glacial acetic acid 20/4/2): Rf value 0.44.
IR: 3600, 3460 (wide), 2998, 2930, 2860, 1740, 1710, 1600, 1590, 1497 cm$^{-1}$.

The NMR spectrum did not show any olefinic protons.

EXAMPLE 14

(13E)-(8R,9S,12R,15S)-9,15-Dihydroxy-11-oxo-16-phenoxy-17,18,19,20-tetranor-prostenoic Acid A solution of 200 mg. of the compound prepared in accordance with Example 1 was shaken under a hydrogen atmosphere at −20° in 20 ml. of ethyl acetate with 20 mg. of palladium (10% on charcoal); the course of the hydrogenation reaction was controlled by thin-layer chromatography. After 1.5 hours, the mixture was purged with nitrogen, filtered, and evaporated under vacuum. After chromatography on silica gel with chloroform/isopropanol (9+1), 154 mg. of the title compound was obtained as a colorless oil.

IR: 3600, 3460 (wide), 2998, 2930, 2860, 1740, 1710, 1600, 1590, 1496, 970 cm$^{-1}$.

EXAMPLE 15

Analogously to Example 14, the following prostenoic acids were obtained from the compounds described in Examples 2–4 and 6–10 by partial hydrogenation:

(13E)-(8R,9S,12R,15S)-9,15-dihydroxy-11-oxo-17-phenyl-18,19,20-trinor-prostenoic acid
(13E)-(8R,9S,12R,15R)-9,15-dihydroxy-11-oxo-16-phenoxy-17,18,19,20-tetranor-prostenoic acid
(13E)-(8R,9S,12R,15R)-9,15-dihydroxy-11-oxo-17-phenyl-18,19,20-trinor-prostenoic acid
(13E)-(8R,9S,12R,15S)-9,15-dihydroxy-11-oxo-16-(4-chlorophenoxy)-17,18,19,20-tetranor-prostenoic acid
(13E)-(8R,9S,12R,15S)-9,15-dihydroxy-11-oxo-16-(3-trifluoromethylphenoxy)-17,18,19,20-tetranor-prostenoic acid
(13E)-(8R,9S,12R,15S)-9,15-dihydroxy-11-oxo-16-(4-fluorophenoxy)-17,18,19,20-tetranor-prostenoic acid
(13E)-(8R,9S,12R,15S)-9,15-dihydroxy-11-oxo-16-(3-chlorophenoxy)-17,18,19,20-tetranor-prostenoic acid
(13E)-(8R,9S,12R,15R)-9,15-dihydroxy-11-oxo-15-(4-chlorophenyl)-16,17,18,19,20-pentanor-prostenoic acid.

EXAMPLE 16

Methyl Ester of (5Z,13E)-(8R,9S,12R,15S)-9,15-Dihydroxy-11-oxo-16-phenoxy-17,18,19,20-tetranor-prostadienoic Acid 5 ml. of an ethereal diazomethane solution (prepared in accordance with "Organikum" p. 528, Berlin, 1965 publishers: Deutscher Verlag der Wissenschaften) was added dropwise to a solution of 500 mg. of the prostadienoic acid obtained according to Example 1 in 25 ml. of methylene chloride. After 3 minutes, the mixture was evaporated under vacuum and filtered over silica gel. With ether/dioxane (95+5), 482 mg. of the title compound is obtained as a colorless oil.

TLC (ether): Rf value 0.30.
IR: 3600, 3300, 2998, 2930, 2860, 1735, 1600, 1588, 1497, 974 cm$^{-1}$.

EXAMPLE 17

Analogously to Example 16, the following compounds were obtained from the prostaglandin acid described in Examples 2–15; the methyl ester of each of the following:

(5Z,13E)-(8R,9S,12R,15S)-9,15-dihydroxy-11-oxo-17-phenyl-18,19,20-trinor-prostadienoic acid
(5Z,13E)-(8R,9S,12R,15R)-9,15-dihydroxy-11-oxo-16-phenoxy-17,18,19,20-tetranor-prostadienoic acid
(5Z,13E)-(8R,9S,12R,15R)-9,15-dihydroxy-11-oxo-17-phenyl-18,19,20-trinor-prostadienoic acid
(5Z)-(8R,9S,12R,15S)-9,15-dihydroxy-11-oxo-16-phenoxy-17,18,19,20-tetranor-prostenoic acid
(5Z,13E)-(8R,9S,12R,15S)-9,15-dihydroxy-11-oxo-16-(4-chlorophenoxy)-17,18,19,20-tetranor-prostadienoic acid (5Z,13E)-(8R,9S,12R,15S)-9,15-dihydroxy-11-oxo-16-(3-trifluoromethylphenoxy)-17,18,19,20-tetranor-prostadienoic acid
(5Z,13E)-(8R,9S,12R,15S)-9,15-dihydroxy-11-oxo-16-(4-fluorophenoxy)-17,18,19,20-tetranor-prostadienoic acid
(5Z,13E)-(8R,9S,12R,15S)-9,15-dihydroxy-11-oxo-16-(3-chlorophenoxy)-17,18,19,20-tetranor-prostadienoic acid
(5Z,13E)-(8R,9S,12R,15R)-9,15-dihydroxy-11-oxo-15-(4-chlorophenyl)-16,17,18,19,20-pentanor-prostadienoic acid
(5Z)-(8R,9S,12R,15R)-9,15-dihydroxy-11-oxo-16-phenoxy-17,18,19,20-tetranor-prostenoic acid
(5Z,13E)-(8R,9S,12R,15R)-9,15-dihydroxy-11-oxo-16-(4-chlorophenoxy)-17,18,19,20-tetranor-prostadienoic acid
(5Z,13E)-(8R,9S,12R,15R)-9,15-dihydroxy-11-oxo-16-(3-trifluoromethylphenoxy)-17,18,19,20-tetranor-prostadienoic acid
(5Z,13E)-(8R,9S,12R,15R)-9,15-dihydroxy-11-oxo-16-(4-fluorophenoxy)-17,18,19,20-tetranor-prostadienoic acid
(5Z,13E)-(8R,9S,12R,15R)-9,15-dihydroxy-11-oxo-16-(3-chlorophenoxy)-17,18,19,20-tetranor-prostadienoic acid
(5Z,13E)-(8R,9S,12R,15S)-9,15-dihydroxy-11-oxo-15-(4-chlorophenyl)-16,17,18,19,20-pentanor-prostadienoic acid
(5Z,13E)-(8R,9S,12R,15S)-9,15-dihydroxy-11-oxo-16-(3-fluorophenoxy)-17,18,19,20-tetranor-prostadienoic acid
(5Z,13E)-(8R,9S,12R,15R)-9,15-dihydroxy-11-oxo-16-(3-fluorophenoxy)-17,18,19,20-tetranor-prostadienoic acid
(5Z,13E)-(8R,9S,12R,15S)-9,15-dihydroxy-11-oxo-17-(4-fluorophenyl)-18,19,20-trinor-prostadienoic acid
(5Z,13E)-(8R,9S,12R,15R)-9,15-dihydroxy-11-oxo-17-(4-fluorophenyl)-18,19,20-trinor-prostadienoic acid
(5Z,13E)-(8R,9S,12R,15S)-9,15-dihydroxy-11-oxo-16-phenoxy-17,18,19,20-tetranor-prostadienoic acid
(8R,9S,12R,15S)-9,15-dihydroxy-11-oxo-16-phenoxy-17,18,19,20-tetranor-prostanoic acid
(13E)-(8R,9S,12R,15S)-9,15-dihydroxy-11-oxo-16-phenoxy-17,18,19,20-tetranor-prostenoic acid
(13E)-(8R,9S,12R,15S)-9,15-dihydroxy-11-oxo-17-phenyl-18,19,20-trinor-prostenoic acid
(13E)-(8R,9S,12R,15R)-9,15-dihydroxy-11-oxo-16-phenoxy-17,18,19,20-tetranor-prostenoic acid
(13E)-(8R,9S,12R,15R)-9,15-dihydroxy-11-oxo-17-phenyl-18,19,20-trinor-prostenoic acid
(13E)-(8R,9S,12R,15S)-9,15-dihydroxy-11-oxo-16-(4-chlorophenoxy)-17,18,19,20-tetranor-prostenoic acid
(13E)-(8R,9S,12R,15S)-9,15-dihydroxy-11-oxo-16-(3-trifluoromethylphenoxy)-17,18,19,20-tetranor-prostenoic acid
(13E)-(8R,9S,12R,15S)-9,15-dihydroxy-11-oxo-16-(4-fluorophenoxy)-17,18,19,20-tetranor-prostenoic acid
(13E)-(8R,9S,12R,15S)-9,15-dihydroxy-11-oxo-16-(3-chlorophenoxy)-17,18,19,20-tetranor-prostenoic acid
(13E)-(8R,9S,12R,15R)-9,15-dihydroxy-11-oxo-15-(4-chlorophenyl)-16,17,18,19,20-pentanor-prostenoic acid.

Replacing the diazomethane used in Example 16 by diazoethane, diazobutane, or diazodecane leads to the corresponding ethyl, butyl, or decyl esters.

EXAMPLE 18 p-Phenylphenacyl Ester of (5Z,13E)-(8R,9S,12R,15S)-9,15-Dihydroxy-11-oxo-16-phenoxy-17,18,19,20-tetranor-prostadienoic Acid 194 mg. of the prostadienoic acid obtained according to Example 1 was agitated with 55 mg. of triethylamine and 150 mg. of p-phenylphenacyl bromide in 12 ml. of acetone for 12 hours at room temperature under argon. After dilution with water, the mixture was extracted with ether, the ether extract was shaken with NaCl solution, dried over magnesium sulfate, and evaporated under vacuum. After chromatographing the residue on silica gel with ether/dioxane (9+1), 161 mg. of the title compound was obtained as a waxy mass.

TLC (ether): Rf value 0.35.

IR: 3600, 3300, 2998, 2930, 2860, 1735, 1690, 1595, 1497, 975 cm$^{-1}$.

EXAMPLE 19

Analogously to Example 18, the following compounds were obtained from the prostaglandin acids described in Examples 2–15; the p-phenylphenacyl ester of each of the following:
(5Z,13E)-(8R,9S,12R,15S)-9,15-dihydroxy-11-oxo-17-phenyl-18,19,20-trinor-prostadienoic acid
(5Z,13E)-(8R,9S,12R,15R)-9,15-dihydroxy-11-oxo-16-phenoxy-17,18,19,20-tetranor-prostadienoic acid
(5Z,13E)-(8R,9S,12R,15R)-9,15-dihydroxy-11-oxo-17-phenyl-18,19,20-trinor-prostadienoic acid
(5Z)-(8R,9S,12R,15R)-9,15-dihydroxy-11-oxo-16-phenoxy-17,18,19,20-tetranor-prostenoic acid
(5Z,13E)-(8R,9S,12R,15S)-9,15-dihydroxy-11-oxo-16-(4-chlorophenoxy)-17,18,19,20-tetranor-prostadienoic acid
(5Z,13E)-(8R,9S,12R,15S)-9,15-dihydroxy-11-oxo-16-(3-trifluoromethylphenoxy)-17,18,19,20-tetranor-prostadienoic acid
(5Z,13E)-(8R,9S,12R,15S)-9,15-dihydroxy-11-oxo-16-(4-fluorophenoxy)-17,18,19,20-tetranor-prostadienoic acid
(5Z,13E)-(8R,9S,12R,15S)-9,15-dihydroxy-11-oxo-16-(3-chlorophenoxy)-17,18,19,20-tetranor-prostadienoic acid
(5Z,13E)-(8R,9S,12R,15R)-9,15-dihydroxy-11-oxo-15-(4-chlorophenyl)-16,17,18,19,20-pentanor-prostadienoic acid
(5Z)-(8R,9S,12R,15R)-9,15-dihydroxy-11-oxo-16-phenoxy-17,18,19,20-tetranor-prostenoic acid
(5Z,13E)-(8R,9S,12R,15R)-9,15-dihydroxy-11-oxo-16-(4-chlorophenoxy)-17,18,19,20-tetranor-prostadienoic acid
(5Z,13E)-(8R,9S,12R,15R)-9,15-dihydroxy-11-oxo-16-(3-trifluoromethylphenoxy)-17,18,19,20-tetranor-prostadienoic acid
(5Z,13E)-(8R,9S,12R,15R)-9,15-dihydroxy-11-oxo-16-(4-fluorophenoxy)-17,18,19,20-tetranor-prostadienoic acid
(5Z,13E)-(8R,9S,12R,15R)-9,15-dihydroxy-11-oxo-16-(3-chlorophenoxy)-17,18,19,20-tetranor-prostadienoic acid
(5Z,13E)-(8R,9S,12R,15S)-9,15-dihydroxy-11-oxo-15-(4-chlorophenyl)-16,17,18,19,20-pentanor-prostadienoic acid
(5Z,13E)-(8R,9S,12R,15S)-9,15-dihydroxy-11-oxo-16-(3-fluorophenoxy)-17,18,19,20-tetranor-prostadienoic acid (5Z,13E)-(8R,9S,12R,15R)-9,15-dihydroxy-11-oxo-16-
(3-fluorophenoxy)-17,18,19,20-tetranor-prostadienoic
acid
(5Z,13E)-(8R,9S,12R,15S)-9,15-dihydroxy-11-oxo-17-
(4-fluorophenyl)-18,19,20-trinor-prostadienoic acid
(5Z,13E)-(8R,9S,12R,15R)-9,15-dihydroxy-11-oxo-17-
(4-fluorophenyl)-18,19,20-trinor-prostadienoic acid
(5Z,13E)-(8R,9R,12R,15S)-9,15-dihydroxy-11-oxo-16-
phenoxy-17,18,19,20-tetranor-prostadienoic acid
(8R,9S,12R,15S)-9,15-dihydroxy-11-oxo-16-phenoxy-
17,18,19,20-tetranor-prostanoic acid
(13E)-(8R,9S,12R,15S)-9,15-dihydroxy-11-oxo-16-
phenoxy-17,18,19,20-tetranor-prostenoic acid
(13E)-(8R,9S,12R,15S)-9,15-dihydroxy-11-oxo-17-phe-
nyl-18,19,20-trinor-prostenoic acid
(13E)-(8R,9S,12R,15R)-9,15-dihydroxy-11-oxo-16-
phenoxy-17,18,19,20-tetranor-prostenoic acid
(13E)-(8R,9S,12R,15R)-9,15-dihydroxy-11-oxo-17-phe-
nyl-18,19,20-trinor-prostenoic acid
(13E)-(8R,9S,12R,15S)-9,15-dihydroxy-11-oxo-16-(4-
chlorophenoxy)-17,18,19,20-tetranor-prostenoic acid
(13E)-(8R,9S,12R,15S)-9,15-dihydroxy-11-oxo-16-(3-
trifluoromethylphenoxy)-17,18,19,20-tetranor-pros-
tenoic acid
(13E)-(8R,9S,12R,15S)-9,15-dihydroxy-11-oxo-16-(4-
fluorophenoxy)-17,18,19,20-tetranor-prostenoic acid
(13E)-(8R,9S,12R,15S)-9,15-dihydroxy-11-oxo-16-(3-
chlorophenoxy)-17,18,19,20-tetranor-prostenoic acid
(13E)-(8R,9S,12R,15R)-9,15-dihydroxy-11-oxo-15-(4-
chlorophenyl)-16,17,18,19,20-pentanor-prostenoic
acid.

EXAMPLE 20

(4-Biphenylyl) Ester of
(5Z,13E)-(8R,9S,12R,15S)-9,15-Dihydroxy-11-oxo-16-
phenoxy-17,18,19,20-tetranor-prostadienoic Acid At 0°, 160 mg. of the prostaglandin acid obtained according to Example 1, dissolved in 18 ml. of chloroform, was combined with 160 mg. of dicyclohexylcarbodiimide. The mixture was agitated for one hour at 0°, and then 1.50 g. of 4-phenylphenol and 0.75 ml. of pyridine were added thereto and the mixture agitated for 4 hours at room temperature. The reaction mixture was thereafter filtered over silica gel, thus obtaining with chloroform 72 mg. of the title compound as a colorless, viscous oil.
TLC (ether): Rf value 0.38.
IR: 3600, 3300, 2998, 2930, 2860, 1745 (wide), 1600, 1588, 976 cm$^{-1}$.

EXAMPLE 21

Analogously to Example 20, the following compounds were obtained from the prostaglandin acids described in Examples 2–15: the (4-biphenylyl)ester of each of the following:
(5Z,13E)-(8R,9S,12R,15S)-9,15-dihydroxy-11-oxo-17-
phenyl-18,19,20-trinor-prostadienoic acid
(5Z,13E)-(8R,9S,12R,15R)-9,15-dihydroxy-11-oxo-16-
phenoxy-17,18,19,20-tetranor-prostadienoic acid
(5Z,13E)-(8R,9S,12R,15R)-9,15-dihydroxy-11-oxo-17-
phenyl-18,19,20-trinor-prostadienoic acid
(5Z)-(8R,9S,12R,15S)-9,15-dihydroxy-11-oxo-16-
phenoxy-17,18,19,20-tetranor-prostenoic acid
(5Z,13E)-(8R,9S,12R,15S)-9,15-dihydroxy-11-oxo-16-
(4-chlorophenoxy)-17,18,19,20-tetranor-pros-
tadienoic acid
(5Z,13E)-(8R,9S,12R,15S)-9,15-dihydroxy-11-oxo-16-
(3-trifluoromethylphenoxy)-17,18,19,20-tetranor-
prostadienoic acid
(5Z,13E)-(8R,9S,12R,15S)-9,15-dihydroxy-11-oxo-16-
(4-fluorophenoxy)-17,18,19,20-tetranor-prostadienoic
acid
(5Z,13E)-(8R,9S,12R,15S)-9,15-dihydroxy-11-oxo-16-
(3-chlorophenoxy)-17,18,19,20-tetranor-pros-
tadienoic acid
(5Z,13E)-(8R,9S,12R,15R)-9,15-dihydroxy-11-oxo-15-
(4-chlorophenyl)-16,17,18,19,20-pentanor-pros-
tadienoic acid
(5Z)-(8R,9S,12R,15R)-9,15-dihydroxy-11-oxo-16-
phenoxy-17,18,19,20-tetranor-prostenoic acid
(5Z,13E)-(8R,9S,12R,15R)-9,15-dihydroxy-11-oxo-16-
(4-chlorophenoxy)-17,18,19,20-tetranor-pros-
tadienoic acid
(5Z,13E)-(8R,9S,12R,15R)-9,15-dihydroxy-11-oxo-16-
(3-trifluoromethylphenoxy)-17,18,19,20-tetranor-
prostadienoic acid
(5Z,13E)-(8R,9S,12R,15R)-9,15-dihydroxy-11-oxo-16-
(4-fluorophenoxy)-17,18,19,20-tetranor-prostadienoic
acid
(5Z,13E)-(8R,9S,12R,15R)-9,15-dihydroxy-11-oxo-16-
(3-chlorophenoxy)-17,18,19,20-tetranor-pros-
tadienoic acid
(5Z,13E)-(8R,9S,12R,15S)-9,15-dihydroxy-11-oxo-15-
(4-chlorophenyl)-16,17,18,19,20-pentanor-pros-
tadienoic acid
(5Z,13E)-(8R,9S,12R,15S)-9,15-dihydroxy-11-oxo-16-
(3-fluorophenoxy)-17,18,19,20-tetranor-prostadienoic
acid
(5Z,13E)-(8R,9S,12R,15R)-9,15-dihydroxy-11-oxo-16-
(3-fluorophenoxy)-17,18,19,20-tetranor-prostadienoic
acid
(5Z,13E)-(8R,9S,12R,15S)-9,15-dihydroxy-11-oxo-17-
(4-fluorophenyl)-18,19,20-trinor-prostadienoic acid
(5Z,13E)-(8R,9S,12R,15R)-9,15-dihydroxy-11-oxo-17-
(4-fluorophenyl)-18,19,20-trinor-prostadienoic acid
(5Z,13E)-(8R,9R,12R,15S)-9,15-dihydroxy-11-oxo-16-
phenoxy-17,18,19,20-tetranor-prostadienoic acid
(8R,9S,12R,15S)-9,15-dihydroxy-11-oxo-16-phenoxy-
17,18,19,20-tetranor-prostanoic acid
(13E)-(8R,9S,12R,15S)-9,15-dihydroxy-11-oxo-16-
phenoxy-17,18,19,20-tetranor-prostenoic acid
(13E)-(8R,9S,12R,15S)-9,15-dihydroxy-11-oxo-17-phe-
nyl-18,19,20-trinor-prostenoic acid
(13E)-(8R,9S,12R,15R)-9,15-dihydroxy-11-oxo-16-
phenoxy-17,18,19,20-tetranor-prostenoic acid
(13E)-(8R,9S,12R,15R)-9,15-dihydroxy-11-oxo-17-phe-
nyl-18,19,20-trinor-prostenoic acid
(13E)-(8R,9S,12R,15S)-9,15-dihydroxy-11-oxo-16-(4-
chlorophenoxy)-17,18,19,20-tetranor-prostenoic acid
(13E)-(8R,9S,12R,15S)-9,15-dihydroxy-11-oxo-16-(3-
trifluoromethylphenoxy)-17,18,19,20-tetranor-pros-
tenoic acid
(13E)-(8R,9S,12R,15S)-9,15-dihydroxy-11-oxo-16-(4-
fluorophenoxy)-17,18,19,20-tetranor-prostenoic acid
(13E)-(8R,9S,12R,15S)-9,15-dihydroxy-11-oxo-16-(3-
chlorophenoxy)-17,18,19,20-tetranor-prostenoic acid
(13E)-(8R,9S,12R,15R)-9,15-dihydroxy-11-oxo-15-(4-
chlorophenyl)-16,17,18,19,20-pentanor-prostenoic
acid By replacing the p-phenylphenol utilized in Example 20 by p-chlorophenol, the corresponding p-chlorophenyl esters are obtained.

EXAMPLE 22

Tris(hydroxymethyl)aminomethane Salt of (5Z,13E)-(8R,9S,12R,15S)-9,15-Dihydroxy-11-oxo-16-phenoxy-17,18,19,20-tetranor-prostadienoic Acid At 80°, a solution of 61 mg. of tris(hydroxymethyl)aminomethane in 0.2 ml. of water was added under agitation to a solution of 195 mg. of the prostaglandin acid produced according to Example 1 in 30 ml. of acetonitrile. The reaction mixture was allowed to stand for 16 hours at room temperature. After vacuum-filtering, 170 mg. of the title compound was obtained as a colorless powder.

EXAMPLE 23

In analogy to Example 22, the following tris(hydroxymethyl)aminomethane salts were obtained from the prostaglandin acids described in Examples 2-15: the tris(hydroxymethyl)aminomethane salt of each of the following:

(5Z,13E)-(8R,9S,12R,15S)-9,15-dihydroxy-11-oxo-17-phenyl-18,19,20-trinor-prostadienoic acid
(5Z,13E)-(8R,9S,12R,15R)-9,15-dihydroxy-11-oxo-16-phenoxy-17,18,19,20-tetranor-prostadienoic acid
(5Z,13E)-(8R,9S,12R,15R)-9,15-dihydroxy-11-oxo-17-phenyl-18,19,20-trinor-prostadienoic acid
(5Z)-(8R,9S,12R,15S)-9,15-dihydroxy-11-oxo-16-phenoxy-17,18,19,20-tetranor-prostenoic acid
(5Z,13E)-(8R,9S,12R,15S)-9,15-dihydroxy-11-oxo-16-(4-chlorophenoxy)-17,18,19,20-tetranor-prostadienoic acid
(5Z,13E)-(8R,9S,12R,15S)-9,15-dihydroxy-11-oxo-16-(3-trifluoromethylphenoxy)-17,18,19,20-tetranor-prostadienoic acid
(5Z,13E)-(8R,9S,12R,15S)-9,15-dihydroxy-11-oxo-16-(4-fluorophenoxy)-17,18,19,20-tetranor-prostadienoic acid
(5Z,13E)-(8R,9S,12R,15S)-9,15-dihydroxy-11-oxo-16-(3chlorophenoxy)-17,18,19,20-tetranor-prostadienoic acid
(5Z,13E)-(8R,9S,12R,15R)-9,15-dihydroxy-11-oxo-15-(4-chlorophenyl)-16,17,18,19,20-pentanor-prostadienoic acid
(5Z)-(8R,9S,12R,15R)-9,15-dihydroxy-11-oxo-16-phenoxy-17,18,19,20-tetranor-prostenoic acid
(5Z,13E)-(8R,9S,12R,15R)-9,15-dihydroxy-11-oxo-16-(4-chlorophenoxy)-17,18,19,20-tetranor-prostadienoic acid
(5Z,13E)-(8R,9S,12R,15R)-9,15-dihydroxy-11-oxo-16-(3-trifluoromethylphenoxy)-17,18,19,20-tetranor-prostadienoic acid
(5Z,13E)-(8R,9S,12R,15R)-9,15-dihydroxy-11-oxo-16-(4-fluorophenoxy)-17,18,19,20-tetranor-prostadienoic acid
(5Z,13E)-(8R,9S,12R,15R)-9,15-dihydroxy-11-oxo-16-(3-chlorophenoxy)-17,18,19,20-tetranor-prostadienoic acid
(5Z,13E)-(8R,9S,12R,15S)-9,15-dihydroxy-11-oxo-15-(4-chlorophenyl)-16,17,18,19,20-pentanor-prostadienoic acid
(5Z,13E)-(8R,9S,12R,15S)-9,15-dihydroxy-11-oxo-16-(3-fluorophenoxy)-17,18,19,20-tetranor-prostadienoic acid
(5Z,13E)-(8R,9S,12R,15R)-9,15-dihydroxy-11-oxo-16-(3-fluorophenoxy)-17,18,19,20-tetranor-prostadienoic acid
(5Z,13E)-(8R,9S,12R,15S)-9,15-dihydroxy-11-oxo-17-(4-fluorophenyl)-18,19,20-trinor-prostadienoic acid
(5Z,13E)-(8R,9S,12R,15R)-9,15-dihydroxy-11-oxo-17-(4-fluorophenyl)-18,19,20-trinor-prostadienoic acid
(5Z,13E)-(8R,9R,12R,15S)-9,15-dihydroxy-11-oxo-16-phenoxy-17,18,19,20-tetranor-prostadienoic acid
(8R,9S,12R,15S)-9,15-dihydroxy-11-oxo-16-phenoxy-17,18,19,20-tetranor-prostanoic acid
(13E)-(8R,9S,12R,15S)-9,15-dihydroxy-11-oxo-16-phenoxy-17,18,19,20-tetranor-prostenoic acid
(13E)-(8R,9S,12R,15S)-9,15-dihydroxy-11-oxo-17-phenyl-18,19,20-trinor-prostenoic acid
(13E)-(8R,9S,12R,15R)-9,15-dihydroxy-11-oxo-16-phenoxy-17,18,19,20-tetranor-prostenoic acid
(13E)-(8R,9S,12R,15R)-9,15-dihydroxy-11-oxo-17-phenyl-18,19,20-trinor-prostenoic acid
(13E)-(8R,9S,12R,15S)-9,15-dihydroxy-11-oxo-16-(4-chlorophenoxy)-17,18,19,20-tetranor-prostenoic acid
(13E)-(8R,9S,12R,15S)-9,15-dihydroxy-11-oxo-16-(3-trifluoromethylphenoxy)-17,18,19,20-tetranor-prostenoic acid
(13E)-(8R,9S,12R,15S)-9,15-dihydroxy-11-oxo-16-(4-fluorophenoxy)-17,18,19,20-tetranor-prostenoic acid
(13E)-(8R,9S,12R,15S)-9,15-dihydroxy-11-oxo-16-(3-chlorophenoxy)-17,18,19,20-tetranor-prostenoic acid
(13E)-(8R,9S,12R,15R)-9,15-dihydroxy-11-oxo-15-(4-chlorophenyl)-16,17,18,19,20-pentanor-prostenoic acid.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11-oxoprostaglandin acid of the formula

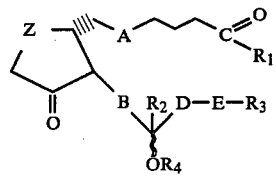

wherein $R_1$ is $-OR_5$, $-NHSO_2CH_3$ or $-O-CH_2-U-V$, $R_5$ being a hydrogen atom, alkyl of 1-10 carbon atoms, monocyclic or bicyclic hydrocarbon aryl of 6-10 ring carbon atoms or a corresponding aryl substituted by 1-3 halogen atoms, phenyl, 1-3 alkyl groups each of 1-4 carbon atoms, chloromethyl, fluoromethyl, trifluoromethyl, carboxyl or hydroxy, or a 5- or 6-member heterocycle group attached by a ring carbon atom thereof and having at least one nitrogen, oxygen or sulfur atom as a ring member, U being a direct bond, carbonyl or carbonyloxy, and V being a phenyl ring substituted by one or more of phenyl, alkoxy or 1-2 carbon atoms, and halogen;

$R_2$ is a hydrogen atom or alkyl of 1-5 carbon atoms;

$R_3$ is alkyl of 1-5 carbon atoms, hydrocarbon alkylaryl of up to 10 carbon atoms wherein aryl is as defined hereinabove, cycloalkyl, aryl as defined hereinabove or benzodioxol-2-yl;

—$OR_4$ is a free or etherified hydroxy group;

A is —$CH_2$—$CH_2$—, cis-CH=CH—, or trans-CH=CH—;

B is —$CH_2$—$CH_2$— or trans-CH=CH—;

D and E collectively are a direct bond, or D is straight-chain or branched alkylene of 1–5 carbon atoms and E is an oxygen or sulfur atom; and Z is >CH ⁓ $OR_4$-group, wherein $OR_4$ can be in the α- or β-position and is as defined above; with the proviso that when D is alkylene and E is an oxygen atom, $R_3$ is alkylaryl of up to 10 carbon atoms, cycloalkyl, aryl or benzodioxolyl-2-yl;

and, when $R_1$ is hydroxy, physiologically acceptable salts thereof with bases.

2. (5Z,13E)-(8R,9S,12R,15S)-9,15-Dihydroxy-11-oxo-17-phenyl-18,19,20-trinor-prostadienoic acid, a compound of claim 1.

3. (5Z,13E)-(8R,9S,12R,15R)-9,15-Dihydroxy-11-oxo-17-phenyl-18,19,20-trinor-prostadienoic acid, a compound of claim 1.

4. (5Z,13E)-(8R,9S,12R,15R)-9,15-Dihydroxy-11-oxo-15-(4-chlorophenyl)-16,17,18,29,20-pentanor-prostadienoic acid, a compound of claim 1.

5. (5Z,13E)-(8R,9S,12R,15R)-9,15-Dihydroxy-11-oxo-15-(4-chlorophenyl)-16,17,18,19,20-pentanor-prostadienoic acid, a compound of claim 1.

6. (5Z,13E)-(8R,9S,12R,15S)-9,15-Dihydroxy-11-oxo-17-(4-fluorophenyl)-18,19,20-trinor-prostadienoic acid, a compound of claim 1.

7. (5Z,13E)-(8R,9S,12R,15R)-9,15-Dihydroxy-11-oxo-17-(4-fluorophenyl)-18,19,20-trinor-prostadienoic acid, a compound of claim 1.

8. (13E)-(8R,9S,12R,15S)-9,15-Dihydroxy-11-oxo-17-phenyl-18,19,20-trinor-prostenoic acid, a compound of claim 1.

9. (13E)-(8R,9S,12R,15R)-9,15-Dihydroxy-11-oxo-17-phenyl-18,19,20-trinor-prostenoic acid, a compound of claim 1.

10. (13E)-(8R,9S,12R,15R)-9,15-Dihydroxy-11-oxo-15-(4-chlorophenyl)-16,17,18,19,20-pantanor-prostenoic acid, a compound of claim 1.

11. p-Phenylphenacyl ester of (5Z,13E)-(8R,9S,12R,15S)-9,15-dihydroxy-11-oxo-16-phenoxy-17,18,19,20-tetranor-prostadienoic acid, a compound of claim 1.

12. (4-Biphenylyl) ester of (5Z,13E)-(8R,9S,12R,15S)-9,15-dihydroxy-11-oxo-16-phenoxy-17,18,19,20-tetranor-prostadienoic acid, a compound of claim 1.

13. Tris(hydroxymethyl)aminomethane salt of (5Z,13E)-(8R,9S,12R,15S)-9,15-dihydroxy-11-oxo-16-phenoxy-17,18,19,20-tetranor-prostadienoic acid, a compound of claim 1.

14. A 9,15-dihydroxy-11-oxoprostaglandin acid or a physiologically acceptable amine salt thereof of claim 1.

15. An alkyl ester of 1–6 carbon atoms of a 9,15-dihydroxy-11-oxoprostaglandin acid of claim 1.

16. A 4-phenylphenylyl ester of a 9,15-dihydroxy-11-oxoprostaglandin acid of claim 1.

17. A p-phenylphenacyl ester of a 9,15-dihydroxy-11-oxoprostaglandin acid of claim 1.

18. A pharmaceutical composition in unit dosage form comprising a compound of claim 1 in admixture with a pharmaceutically acceptable carrier.

* * * * *